United States Patent [19]

Hagen et al.

[11] Patent Number: 5,177,286

[45] Date of Patent: * Jan. 5, 1993

[54] SELECTIVE PRODUCTION OF A P-ALKYLTOLUENE OR 4,4'-ALKYLMETHYLBIPHENYL

[75] Inventors: Gary P. Hagen, West Chicago, Ill.; Deborah T. Hung, Cambridge, Mass.

[73] Assignee: Amoco Corporation, Chicago, Ill.

[*] Notice: The portion of the term of this patent subsequent to Dec. 15, 2009 has been disclaimed.

[21] Appl. No.: 544,270

[22] Filed: Jun. 26, 1990

[51] Int. Cl.⁵ .............................................. C07C 5/22
[52] U.S. Cl. .................................. 585/472; 585/471; 585/474
[58] Field of Search .................. 585/471, 472, 474

[56] References Cited

U.S. PATENT DOCUMENTS

| | | | |
|---|---|---|---|
| 2,388,758 | 11/1945 | Mills, Jr. | 585/474 |
| 4,454,364 | 6/1984 | Farcasiu et al. | 585/472 |
| 4,873,386 | 10/1989 | Hagen et al. | 585/472 |
| 4,950,824 | 8/1990 | Shiroto et al. | 585/474 |

FOREIGN PATENT DOCUMENTS 0116353 10/1978 Japan.

Primary Examiner—Patrick P. Garvin
Assistant Examiner—E. D. Irzinski
Attorney, Agent, or Firm—Thomas E. Nemo; Wallace L. Oliver; Frank J. Sroka

[57] ABSTRACT

A method for the highly selective production of a p-alkyltoluene or 4,4'-alkylmethylbiphenyl involving the use of a specific Lewis acid catalyst and a highly regeospecific methylating agent.

16 Claims, No Drawings

SELECTIVE PRODUCTION OF A P-ALKYLTOLUENE OR 4,4'-ALKYLMETHYLBIPHENYL

BACKGROUND OF THE INVENTION

1. Field of the Invention

This invention relates generally to the production of a p-alkyltoluene or a 4,4'-alkylmethylbiphenyl and more particularly concerns the highly selective production of p-xylene or p-ethyltoluene by the transmethylation of benzene, toluene or ethylbenzene or the production of 4,4'-dimethyl- or -methylethylbiphenyl by the transmethylation of biphenyl, 4-methylbiphenyl or 4-ethylbiphenyl.

2. Description of the Prior Art

Dialkylbiphenyls are useful as high temperature heat transfer media. Dialkylbiphenyls, as well as dialkylbenzenes, are also desirable feedstocks for oxidation to the corresponding biphenyl or benzene dicarboxylic acids, which in turn are monomers that are known to be useful for the preparation of a variety of polymers. A known conventional process for producing a benzene dicarboxylic acid or a biphenyl dicarboxylic acid comprises the oxidation of a dialkylbenzene or a dialkylbiphenyl, respectively, with oxygen in the liquid phase in an acetic acid solvent at an elevated temperature and pressure and in the presence of a catalyst comprising cobalt, manganese and bromine components. In such cases, it is highly desirable that the alkyl groups on the benzene or biphenyl ring are methyl or ethyl.

Thus, there is a need for p-dialkylbenzenes and 4,4'-dialkylbiphenyls and for highly selective processes for making specific p-dialkylbenzenes or 4,4'-dialkylbiphenyls. Because of the great difficulty and expense of separating one p-dialkylbenzene or one 4,4'-dialkylbiphenyl from its other dialkylbenzene isomers or other dialkylbiphenyl isomers, respectively, methods for producing a specific p-dialkylbenzene or a specific 4,4'-dialkylbiphenyl in high purity and quality are especially desirable. One such method is disclosed in Japanese Kokai Patent Application Publication No. 62-252733 (Nov. 4, 1987) and is a process for the transethylation of biphenyl with an ethylbenzene or ethyltoluene to form monoethylbiphenyl and diethylbiphenyl in the presence of a Friedel-Crafts catalyst, such as aluminum chloride at 70°-150° C. This published Japanese patent application discloses that reaction temperatures of less than 70° C. delay the reaction rate. The ring positions of the ethyl substituents in the ethylated biphenyl products are not disclosed. Suitable ethylbenzenes and ethyltoluenes include ethylbenzene, diethylbenzene, triethylbenzene, tetraethylbenzene, other ethyl-substituted benzenes, ethyltoluene diethyltoluene and other ethyl-substituted toluenes. Polyethylbenzenes containing relatively small amounts of monoethylbenzene, triethylbenzene and tetraethylbenzene can also be used advantageously.

Japanese Patent Application 261336, published on Oct. 18, 1989, discloses a method for the preparation of ethyldiphenylethane or diethyldiphenylethane by the transethylation of diphenylethane with polyethylbenzene(s) in the presence of a Friedel-Crafts catalyst at 0°-150° C. Preferred catalysts are aluminum chloride, aluminum bromide and boron trifluoride. Transethylation of 1,1-diphenylethane by this method produces either 1-phenyl-1-ethylphenylethane, 1-phenyl-1-diethylphenylethane or 1,1-bis(ethylphenyl)ethane. The ring positions of the ethyl substituents in the ethylated products are not disclosed.

With regard to a different aromatic ring system, Olah et al., "Alkylation of Naphthalene with Alkyl Halides," Journal of American Chemical Society, 98:7, pages 1839-1842 (Mar. 31, 1976), disclose that theretofor there was no clear understanding of directive effects and selectivities for the Friedel-Crafts alkylation of naphthalene. Olah et al. discloses poor selectivities and/or low conversions for the direct methylation of naphthalene or 2-methylnaphthalene using simple methylating agents such as methyl halides or methanol to provide beta-substituted products such as 2,6-dimethylnaphthalenes.

Since then, Japanese Kokai Patent Application Publication No. 61-83137 (Apr. 26, 1986) discloses a synthesis involving the transalkylation of naphthalene or a 2-methylnaphthalene in the presence of an aluminum chloride catalyst at 0°-35° C. in the liquid phase to produce a 2,6-dialkylnaphthalene. Suitable alkylating agents are disclosed as including durene, diethylbenzene, triethylbenzene, triisopropylbenzene, isopropylxylene, and dibutylbenzene. The reported results indicate a relatively low degree of selectivity for the formation of specific stated that the disclosed alkylation method must be performed at 0°-35° C., preferably room temperature, and that the higher the reaction temperature, the lower the selectivity for beta-alkylsubstituted naphthalene and especially 2,6-dialkylnaphthalene. In addition, although this patent application publication specifically mentions durene (1,2,4,5-tetramethylbenzene) as an example of an alkylation agent, it contains actual examples that illustrate only the use as alkylating agents in the method disclosed therein of polyalkylbenzenes where the alkyl groups are larger than methyl groups and indicates as follows that polyalkylbenzenes with alkyl groups other than methyl groups afford benefits in the method disclosed therein: "Polyalkylbenzenes with ethyl, propyl, or butyl groups with high-carbon alkyl groups have high reaction rates . . . ." Moreover, this published Japanese patent application states that when the naphthalene is solid at the reaction temperature, a solvent such as a paraffin or cycloparaffin should be employed. This published patent application publication discusses the use of halogenated alkyl in the alkylation of naphthalenes as a prior art method which did not produce a beta-alkyl naphthalene with the desired selectivity.

Shimada et al., "Ethylation and Transethylation of Naphthalene," Bulletin of the Chemical Society of Japan, Vol. 48 (II), pages 3306-3308 (Nov. 1975), disclose the transethylation of naphthalene by ethylbenzene or ethylxylenes to form monoethylnaphthalenes in the presence of an aluminum chloride catalyst at 20°-30° C. The rates of transethylation with ethylxylene isomers were reported to decrease in the order of 1,2-dimethyl-4-ethylbenzene ≧ 1,3-dimethyl-4-ethylbenzene ≧ 1,4-dimethyl-2-ethylbenzene ≧ 1,3-dimethyl-5-ethylbenzene.

Thus, until recently, no existing method was known for the highly selective production of 2,6diethylnaphthalene or a mixture of 2,6- and 2,7diethylnaphthalenes by a transethylation process. Then Hagen et al., U.S. Pat. No. 4,873,386, which issued on Oct. 10, 1989, disclose a method for producing 2,6-diethylnaphthalene which comprises: reacting in the liquid phase at least one of naphthalene or 2ethylnaphthalene as the feed with at least one of 1,4-diethylbenzene, 1,2,4-triethylbenzene, or at least one tetraethylbenzene or pentaethylbenzene as the ethylating agent per mole of the feed, in the presence of a Lewis acid catalyst selected from the group consisting of aluminum chloride, aluminum bromide, boron trichloride, tantalum pentachloride, antimony pentafluoride, and red oil at a level of from about 0.01 to about 1 mole of the catalyst (for red oil, based on the aluminum chloride content of the red oil) per mole of the feed and at a temperature in the range of from about −10° C. to about 100° C. In particular, Hagen et al., disclose that 1,2,3,4- and 1,2,3,5-tetraethylbenzenes, as well as 1,2,4,5tetraethylbenzene (durene), are useful ethylating agents, but that hexaethylbenzene is not. Hagen et al. further disclose that 2,6-diethylnaphthalene is formed at a higher selectivity and yield when 2-ethylnaphthalene is transethylated and that pentaethylbenzene and any tetraethylbenzene are the preferred ethylating agents. However, Hagen et al. neither disclose nor suggest that the method disclosed therein would be useful for the selective methylation to produce p-alkyltoluene or 4,4'-alkylmethylbiphenyl.

OBJECTS OF THE INVENTION

It is therefore a general object of the present invention to provide an improved method for the highly selective production of p-alkyltoluene or 4,4'-alkylmethylbiphenyl.

More specifically, it is an object of the present invention to provide an improved method for the highly selective production of p-ethyltoluene, p-xylene, 4,4'-dimethylbiphenyl, or 4,4'-methylethylbiphenyl by methylation under highly regeospecific conditions.

Other objects and advantages of the invention will become apparent upon reading the following detailed description and appended claims.

SUMMARY OF THE INVENTION

These objects are achieved by an improved method for producing (a) p-alkyltoluene, where the alkyl group is methyl or ethyl, from benzene, toluene, ethylbenzene, or a mixture of benzene and toluene as the feed or (b) a 4,4'-alkylmethylbiphenyl, where the alkyl group is methyl or ethyl, from biphenyl, 4-methylbiphenyl, 4-ethylbiphenyl, or a mixture of biphenyl and 4-methylbiphenyl as the feed, comprising: reacting the feed in the liquid phase with at least one of 1,2,4,5-tetramethylbenzene, pentamethylbenzene or hexamethylbenzene as the methylating agent, at a level of from about 1 to about 10 moles of the methylating agent per mole of the feed, in the presence of a Lewis acid or Bronsted acid alkylation catalyst or mixture thereof that is more acidic than ferric chloride and at least as acidic as ferric bromide, at a level of from about 0.01 to about 1 mole of the catalyst per mole of the feed and at a temperature in the range of from about −40° C. to about 80° C.

DETAILED DESCRIPTION OF THE PREFERRED EMBODIMENTS

Benzene, toluene, ethylbenzene, or a mixture of benzene and toluene is suitable for use as the feed in the method of this invention to make a p-alkyltoluene. Biphenyl, 4-methylbiphenyl, 4-ethylbiphenyl, or a mixture of biphenyl and 4-methylbiphenyl is suitable for use as the feed in the method of this invention to make a 4,4'-alkylmethylbiphenyl. Preferably, a feed comprising toluene or ethylbenzene is employed to make p-alkyltoluene or a feed comprising 4-methylbiphenyl or 4-ethylbiphenyl is employed to make 4,4'alkylmethylbiphenyl in the method of this invention. The feed must be either dissolved in a suitable solvent as described below or must be liquid at the reaction temperature employed.

Relative to the dimethylbenzenes, trimethylbenzenes, and 1,2,3,4- and 1,2,3,5-tetramethylbenzenes, the following afford substantially improved yields of the desired p-alkyltoluene or 4,4'-alkylmethylbiphenyl in the method of this invention and are the only suitable ethylating agents in the method of this invention: 1,2,4,5-tetramethylbenzene (durene), pentamethylbenzene, hexamethylbenzene, and mixtures thereof. The mole ratio of the methylating agent to benzene, toluene, ethylbenzene, biphenyl, 4-methylbiphenyl or 4-ethylbiphenyl, a mixture of benzene and toluene or a mixture of biphenyl and 4-methylbiphenyl is in the range of from about 1:1, preferably from about 2:1, to about 10:1, preferable to about 5:1, in the method of this invention.

The transmethylation reaction of the present invention is conducted in the liquid phase in the presence or absence of a solvent. Any liquid that is inert under the reaction conditions employed and serves as an effective solvent for the reactants and products is suitable for use in the method of this invention. Suitable solvents include halocarbons, such as methylene chloride, chlorobenzene, 1,1-dichloroethane, 1,2-dichloroethane, and chloroform, or carbon disulfide, benzene, cyclohexane, and n-octane. Solvents which are basic and bind irreversibly with the catalyst are not suitable. Such unsuitable solvents include ketones, aldehydes, ethers, esters and alcohols. Preferably, the solvent is methylene chloride. If a solvent is employed, the weight ratio of solvent-to-feed compound is in the range of from about 1:1, preferably from about 2:1, to about 15:1, preferably to about 8:1.

Lewis acids and Bronsted acids or mixtures thereof that are conventionally used as alkylation catalysts and that are more acidic than ferric chloride and at least as acidic as ferric bromide, and preferably at least as acidic as aluminum chloride, and that do not decompose under the conditions employed in the method of this invention are suitable for use as the catalyst in the method of this invention. Suitable Lewis acid catalysts include aluminum chloride, aluminum bromide, boron trichloride, tantalum pentachloride, antimony pentafluoride, ferric bromide, sulfonated zirconia, trifluoromethanesulfonic acid, and "red oil," a complex polar liquid catalyst phase which is synthesized by addition of ethyl chloride or bromide or hydrogen chloride or bromide to a slurry of aluminum chloride or some other aforesaid suitable Lewis acid in an aromatic solvent such as benzene, methylbenzene, ethylbenzene, mixed dimethylbenzenes, mixed diethylbenzenes, mixed tetramethylbenzenes or mixed tetraethylbenzenes. Preferably, aluminum chloride or red oil-containing aluminum chloride is the catalyst.

The catalyst can be employed as a separate immiscible layer such as the aforementioned red oil, or it can be dissolved with the reactants and products in an organic solvent such as methylene chloride or chlorobenzene. Thus, depending upon the selection of solvent for the catalyst, the feed, ethylating agent and catalyst can be present in a single liquid phase, or the feed and catalyst can be present in separate liquid phases. In the alternative, the catalyst can be in the form of a solid, for example, aluminum chloride deposited or intercalated with graphite. The catalyst is employed in the method of this invention at a level in the range of from about 0.01, preferably from about 0.05, to about 1.0, preferably to about 0.2 mole per mole of the total content of benzene, toluene, ethylbenzene, biphenyl, 4-methylbiphenyl, 4-ethylbiphenyl, or a mixture thereof. In general, the greater the amount of catalyst employed relative to the amount of feed employed, the greater are the rate of the transmethylation and the extent of conversion of the feed.

Other conventional Lewis acids, such as antimony chloride, bismuth chloride, ferric chloride, tin chloride, titanium chloride, and zinc chloride are not such effective catalysts in the method of the present invention.

If the reaction is performed continuously or batchwise, the residence time is from 0.1, preferably from about 1, to about 10, preferably to about 5 hours.

The reaction temperature is in the range of from about −40° C., preferably from about 0° C., to about 80° C., preferably to about 60° C. The reaction pressure must be sufficiently high to maintain the reactants and products in the liquid phase at the particular reaction temperature employed and generally is in the range of from about 0.5, preferably from about 0.8, to about 10, preferably to about 5, atmospheres gauge.

Preferably, when a polar solvent is not used, a hydrogen halide, such as hydrogen chloride, or an alkyl, alkylene or alkylidene halide is employed as a promoter in the method of the present invention. Typically, such alkyl, alkylene, or alkylidene halides include a methyl halide, such as methyl chloride, or a methylene, ethylene, or ethylidine halide. The promoter is employed at a level of from 0.1, preferably from about 0.5, up to about 100, preferably up to at least 2 moles per mole of catalyst (for red oil, based on the aluminum chloride content of the red oil). When the solvent is an alkyl or alkylene halide, it also serves as a promoter in the method of the invention.

The present invention will be more clearly understood from the following specific examples:

EXAMPLES 1–24

Except as indicated hereinbelow, each of Examples 1–24 was performed using a 250 milliliter, 3-neck, round-bottom flask equipped with a magnetic stirrer, purged with nitrogen and cooled in an ice bath. The components of the reaction mixture that are identified in Table 1 were introduced in the amounts and under the reaction conditions specified in Table 1. In each case the catalyst was introduced last, at which point the transmethylation reaction commenced immediately. Twenty-four hours after the catalyst was introduced, methanol, in a volume that was approximately twice the volume of the reaction medium, was generally introduced to quench the reaction. The product mixture was then analyzed to determine the weight percent of biphenyl, 4-methylbiphenyl or toluene (identified as BP, 4-MBP, or TOL, respectively, in Table 1) that is converted ("Conversion"), the "Yield or mole percent of BP, 4-MBP, or TOL, that is converted selectively to 4,4'-dimethylbiphenyl (identified as 4,4'-DMBP in Table 2) or p-xylene, and the "Selectivity" or mole percent of BP, 4-MBP, or TOL in the combined amounts of products produced in each example. The Yield is also the quotient obtained by dividing 100 into the product of the Conversion multiplied by Selectivity.

The results of Examples 3 and 24 illustrate that the method of this invention is effective for the selective substitution in the 4 positions of both the biphenyl and benzenoid systems. Comparison of the results of Examples 16–18 illustrates that iron chloride, a relatively weaker Lewis acid, is less effective in the method of this invention, than are aluminum chloride and aluminum bromide, relatively stronger Lewis acids. Comparison of the results of Examples 14, 16 and 21 illustrates that the use of a catalyst at higher concentration levels affords higher yields and selectivities for the desired product. Comparison of the results of Examples 8, 9, 11, 12 and 13 illustrate that tetramethylbenzene and pentamethylbenzene are more effective methylating agents in the method of this invention than is trimethylbenzene, and comparison of the results of Examples 11 and 12 illustrate that 1,2,4,5-tetramethylbenzene is a more effective, methylating agent in the method of this invention than is 1,2,3,5-tetramethylbenzene.

TABLE 1

| Example No. | Feed | Methylating Agent Compound | Amount[1] | Catalyst Compound | Amount[1] |
|---|---|---|---|---|---|
| 1 | BP | HMB | 1 | AlCl$_3$ | 0.4 |
| 2 | BP | HMB | 1 | AlCl$_3$ | 0.4 |
| 3 | BP | HMB | 1 | AlCl$_3$ | 0.4 |
| 4 | BP | HMB | 1 | AlCl$_3$ | 0.4 |
| 5 | 4-MBP | 1,2,4,5-TeMB | 2 | AlCl$_3$ | 0.4 |
| 6 | 4-MBP | HMB | 1 | AlCl$_3$ | 0.4 |
| 7 | 4-MBP | PMB | 1 | AlCl$_3$ | 1.0 |
| 8 | 4-MBP | PMB | 2 | AlCl$_3$ | 1.0 |
| 9 | 4-MBP | 1,3,5-TMB | 2 | AlCl$_3$ | 1.0 |
| 10 | BP | PMB | 4 | AlCl$_3$ | 1.0 |
| 11 | 4-MBP | 1,2,4-TMB | 2 | AlCl$_3$ | 1.0 |
| 12 | 4-MBP | 1,2,3,5-TeMB | 2 | AlCl$_3$ | 1.0 |
| 13 | 4-MBP | 1,2,4,5-TeMB | 2 | AlCl$_3$ | 1.0 |
| 14 | 4-MBP | 1,2,4,5-TeMB | 3.3 | AlCl$_3$ | 0.83 |
| 15 | 4-MBP | 1,2,4,5-TeMB | 3 | AlCl$_3$ | 0.2 |
| 16 | 4-MBP | 1,2,4,5-TeMB | 2 | AlCl$_3$ | 0.2 |

| Example No. | Reaction Temp. (°) | Solvent Compound | Amount[4] | Promoter Compound | Amount |
|---|---|---|---|---|---|
| 1 | 40 | Pseudocumene | 32/.06 | HCl | Sat'd |
| 2 | 60 | C$_6$H$_{12}$[3] | 180/.06 | HCl | Sat'd |
| 3 | 60 | C$_6$H$_{12}$[3] | 150/.06 | HCl | Sat'd |
| 4 | 70 | C$_6$H$_{12}$[3] | 80/.06 | HCl | Sat'd |
| 5 | 20 | CH$_2$Cl$_2$[2] | 30/.0025 | Solvent | 30/.0025[4] |
| 6 | 70 | C$_6$H$_{12}$[3] | 25/.0029 | HCl | Sat'd |
| 7 | 20 | CH$_2$Cl$_2$[2] | 30/.0025 | Solvent | 30/.0025[4] |
| 8 | 20 | CH$_2$Cl$_2$[2] | 30/.0025 | Solvent | 30/.0025[4] |
| 9 | 20 | CH$_2$Cl$_2$[2] | 30/.0025 | Solvent | 30/.0025[4] |
| 10 | 0 | CH$_2$Cl$_2$[2] | 30/.0025 | Solvent | 30/.0025[4] |
| 11 | 20 | CH$_2$Cl$_2$[2] | 30/.0025 | Solvent | 30/.0025[4] |
| 12 | 20 | CH$_2$Cl$_2$[2] | 30/.0025 | Solvent | 30/.0025[4] |
| 13 | 20 | CH$_2$Cl$_2$[2] | 30/.0025 | Solvent | 30/.0025[4] |
| 14 | 20 | CH$_2$Cl$_2$[2] | 30/.0005 | Solvent | 30/.0005[4] |
| 15 | 20 | CH$_2$Cl$_2$[2] | 30/.0025 | Solvent | 30/.0025[4] |
| 16 | 20 | CH$_2$Cl$_2$[2] | 30/.0025 | Solvent | 30/.0025[4] |

| Example No. | Feed | Methylating Agent Compound | Amount[1] | Catalyst Compound | Amount[1] |
|---|---|---|---|---|---|
| 17 | 4-MBP | 1,2,4,5-TeMB | 2 | AlBr$_3$ | 0.2 |
| 18 | 4-MBP | 1,2,4,5-TeMB | 2 | FeCl$_3$ | 0.2 |
| 19 | BP + 4-MBP | 1,2,4,5-TeMB | 3.3 | AlCl$_3$ | 0.17 |
| 20 | 4-MBP | 1,2,4,5-TeMB | 2 | AlCl$_3$ | 0.2 |
| 21 | BP + 4-MBP | 1,2,4,5-TeMB | 3.3 | AlCl$_3$ | 0.17 |
| 22 | 4-MBP | 1,2,4,5-TeMB | 2 | ZrO$_2$/SO$_4^{-2}$ | 40[5] |
| 23 | BP + 4-MBP | 1,2,4,5-TeMB | 3.3 | ZrO$_2$/SO$_4^{-2}$ | 33.3[5] |

TABLE 1-continued

| | 24 | TOL | HMB | 1 | AlCl₃ | 0.4 |
|---|---|---|---|---|---|---|

| Example No. | Reaction Temp. (°C.) | Solvent Compound | Amount[4] | Promoter Compound | Amount |
|---|---|---|---|---|---|
| 17 | 20 | CH₂Cl₂ | 30/.0025 | solvent | 30/.0025[4] |
| 18 | 20 | CH₂Cl₂ | 30/.0025 | solvent | 30/.0025[4] |
| 19 | 20 | CH₂Cl₂ | 30/.0025 | solvent | 30/.0025 + .0005[4] |
| | | | + .0005 | | |
| 20 | 20 | CH₂Cl₂ | 30/.0025 | solvent | 30/.0025[4] |
| 21 | 20 | CH₂Cl₂ | 30/.0025 | solvent | 30/.0025 + .0005[4] |
| | | | + .0005 | | |
| 22 | 20 | CH₂Cl₂ | 30/.0025 | solvent | 30/.0025[4] |
| 23 | 20 | CH₂Cl₂ | 30/.0025 | solvent | 30/.0025 + .0005[4] |
| | | | + .0005 | | |
| 24 | 50 | C₆H₁₂[3] | 25/.035 | HCl | Sat'd |

Footnotes
[1] moles per mole of feed
[2] dissolves reactants, product and catalyst
[3] dissolves reactants and product, but not catalyst
[4] milliliters of solvent per the actual number of moles of feed used
[5] milligrams per millimole of feed

TABLE 2

| Example No. | Reaction Time (min) | Conversion | 4,4'-DMBP Product Yield | Selectivity |
|---|---|---|---|---|
| 1 | 590 | 1.53 | 0 | 0 |
| 2 | 900 | 2.45 | 0 | 0 |
|  | 1350 | 6.07 | 0 | 0 |
|  | 1650 | 9.21 | 0.32 | 3.51 |
|  | 2190 | 15.26 | 0.91 | 5.95 |
|  | 3720 | 19.46 | 1.51 | 7.77 |
| 3 | 450 | 2.24 | 0 | 0 |
|  | 1560 | 4.93 | 0 | 0 |
|  | 3240 | 12.37 | 0.66 | 5.32 |
|  | 3600 | 17.34 | 1.28 | 7.41 |
|  | 4020 | 22.88 | 2.19 | 9.56 |
| 4 | 450 | 1.59 | 0 | 0 |
|  | 900 | 8.42 | 0.24 | 2.87 |
|  | 1350 | 16.83 | 1.08 | 6.40 |
| 5 | 30 | 10.10 | 10.10 | 100.00 |
|  | 90 | 16.02 | 16.02 | 100.00 |
|  | 180 | 18.33 | 18.33 | 100.00 |
|  | 420 | 19.35 | 19.35 | 100.00 |
| 6 | 60 | 1.92 | 1.08 | 56.52 |
|  | 180 | 6.25 | 5.03 | 80.41 |
|  | 360 | 10.02 | 8.30 | 82.86 |
|  | 1860 | 10.45 | 8.59 | 83.16 |
| 7 | 30 | 4.0 | 2.4 | 59.5 |
|  | 90 | 9.9 | 8.6 | 87.3 |
|  | 240 | 21.2 | 19.9 | 93.9 |
|  | 360 | 30.3 | 28.8 | 95.1 |
| 8 | 30 | 4.6 | 2.6 | 56.4 |
|  | 90 | 13.7 | 12.2 | 88.9 |
|  | 240 | 33.1 | 31.1 | 94.0 |
|  | 560 | 45.6 | 42.3 | 92.8 |
|  | 1440 | 75.5 | 67.0 | 88.7 |
| 9 | 30 | 2.6 | 1.2 | 45.1 |
|  | 120 | 8.2 | 6.2 | 75.4 |
|  | 240 | 17.8 | 15.4 | 86.3 |
| 10 | No reaction | | | |
| 11 | 30 | 9.1 | 6.1 | 67.4 |
|  | 90 | 13.5 | 10.1 | 75.1 |
|  | 180 | 16.0 | 12.2 | 76.6 |
|  | 420 | 19.3 | 15.3 | 79.1 |
|  | 1440 | 22.1 | 17.7 | 80.3 |
| 12 | 30 | 3.7 | 2.3 | 61.1 |
|  | 120 | 11.7 | 10.3 | 88.3 |
|  | 240 | 20.9 | 19.6 | 93.9 |
|  | 420 | 34.1 | 32.5 | 95.2 |
|  | 1440 | 78.7 | 75.2 | 95.4 |
| 13 | 30 | 47.5 | 41.7 | 87.8 |
|  | 90 | 57.7 | 52.0 | 90.1 |
|  | 240 | 70.7 | 63.1 | 89.2 |
|  | 420 | 79.9 | 64.5 | 80.8 |
|  | 1440 | 78.8 | 68.0 | 86.3 |
| 14 | 30 | 28.3 | 26.4 | 93.4 |
|  | 120 | 31.6 | 30.0 | 95.0 |
|  | 240 | 44.6 | 38.2 | 85.7 |
|  | 360 | 53.6 | 41.3 | 77.1 |
|  | 1440 | 86.5 | 66.6 | 77.0 |
| 15 | 30 | 16.4 | 14.5 | 88.3 |
|  | 90 | 25.7 | 23.5 | 91.4 |
|  | 240 | 34.8 | 31.2 | 89.6 |
|  | 360 | 39.0 | 34.8 | 89.2 |
|  | 1440 | 45.6 | 40.2 | 88.3 |
| 16 | 30 | 15.8 | 13.7 | 86.9 |
|  | 120 | 25.7 | 24.0 | 93.5 |
|  | 240 | 37.1 | 35.3 | 95.2 |
|  | 360 | 43.9 | 37.6 | 92.6 |
|  | 1440 | 48.6 | 43.1 | 88.8 |
| 17 | 30 | 15.5 | 13.3 | 86.0 |
|  | 120 | 24.0 | 20.9 | 87.1 |
|  | 240 | 29.6 | 26.0 | 87.7 |
|  | 360 | 32.8 | 29.0 | 88.4 |
|  | 1440 | 36.1 | 31.8 | 88.2 |
| 18 | 1440 | 1.2 | 0.1 | 9.9 |
| 19 | No reaction | | | |
| 20 | 360 | 28.5 | 26.2 | 91.8 |
|  | 1800 | 33.5 | 30.3 | 90.6 |
|  | 3240 | 32.9 | 30.6 | 92.9 |
| 21 | No reaction | | | |
| 22 | No reaction | | | |
| 23 | No reaction | | | |
| 24 | 360 | 3.48 | 2.93 | 84.11 |
|  | 600 | 11.29 | 8.51 | 75.37 |
|  | 840 | 23.14 | 16.21 | 70.05 |
|  | 1140 | 44.73 | 26.86 | 60.04 |
|  | 1650 | 73.56 | 33.39[1] | 45.38[1] |

Footnotes
[1] yield and selectivity for paraxylene

From the above description, it is apparent that the objects of the present invention have been achieved. While only certain embodiments have been set forth, alternative embodiments and various modifications will be apparent from the above description to those skilled in the art. These and other alternatives are considered equivalents and within the spirit and scope of the present invention.

Having described the invention, what is claimed is:

1. A method for producing (a) a p-alkyltoluene, wherein the alkyl group is methyl or ethyl, from benzene, toluene, ethylbenzene, or a mixture of benzene and toluene as the feed or (b) a 4,4'-alkylmethylbiphenyl, wherein the alkyl group is methyl or ethyl, from biphenyl, 4-methylbiphenyl, 4-ethylbiphenyl or a mixture of biphenyl and 4-methylbiphenyl as the feed, comprising: reacting the feed in the liquid phase with at least one of 1,2,4,5-tetramethylbenzene, pentamethylbenzene or hexamethylbenzene as the methylating agent, at a level of from about 1 to about 10 moles of the methylating agent per mole of the feed, in the presence of a catalyst comprising a Lewis acid or Bronsted acid alkylation catalyst or a mixture thereof that is more acidic than ferric chloride and at least as acidic as ferric bromide, at a level of from about 0.01 to about 1 mole of the catalyst per mole of the feed and at a temperature in the range of from about $-40°$ C. to about $80°$ C.

2. The method of claim 1 wherein the feed comprises biphenyl, 4-methylbiphenyl, 4-ethylbiphenyl, or a mixture of biphenyl and 4-methylbiphenyl.

3. The method of claim 1 wherein the feed comprises benzene, toluene, ethylbenzene, or a mixture of benzene and toluene.

4. The method of claim 1 wherein the methylating agent is 1,2,4,5-tetramethylbenzene.

5. The method of claim 1 wherein the methylating agent is at a level of from about 2 to about 5 moles per mole of the feed by weight.

6. The method of claim 1 wherein the catalyst comprises aluminum chloride, aluminum bromide, boron trichloride, tantalum pentachloride, antimony pentafluoride, ferric bromide, sulfonated zirconia, trifluoromethanesulfonic acid or red oil.

7. The method of claim 6 wherein the catalyst comprises red oil or aluminum chloride.

8. The method of claim 1 wherein the catalyst is at a level of from 0.05 to about 0.2 mole per mole of the feed.

9. The method of claim 1 wherein the reaction is conducted at a temperature in the range of from about 0° C. to about 60° C.

10. The method of claim 1 wherein the reaction is conducted in the presence of a promoter comprising a hydrogen halide or an alkyl, alkylene or alkylidene halide, at a level of from about 0.1 to about 100 moles per mole of the catalyst.

11. The method of claim 10 wherein the promoter is hydrogen chloride or methylene chloride.

12. The method of claim 1 wherein the feed and methylating agent are dissolved in a solvent.

13. The method of claim 1 wherein the catalyst is dissolved in a solvent.

14. The method of claim 1 wherein the feed, methylating agent and catalyst are present in a single liquid phase.

15. The method of claim 1 wherein the feed and catalyst are present in separate liquid phases.

16. The method of claim 1 wherein the catalyst is in the solid phase.

* * * * *

UNITED STATES PATENT AND TRADEMARK OFFICE
CERTIFICATE OF CORRECTION

PATENT NO.: 5,177,286

DATED: Jan. 5, 1993

INVENTOR(S): Hagen, Gary P.; Hung, Deborah T.

It is certified that error appears in the above-identified patent and that said Letters Patent is hereby corrected as shown below:

| Col. | Line | |
|---|---|---|
| 2 | 25 | "specific stated" should read --specific dialkylnaphthalenes. Furthermore, it is specifically stated...--. |

Signed and Sealed this

Twenty-fifth Day of January, 1994

Attest:

BRUCE LEHMAN

Attesting Officer

Commissioner of Patents and Trademarks